United States Patent
Heinrich et al.

(10) Patent No.: US 11,116,423 B2
(45) Date of Patent: Sep. 14, 2021

(54) PATIENT MONITORING SYSTEM AND METHOD

(71) Applicant: KONINKLIJKE PHILIPS N.V., Eindhoven (NL)

(72) Inventors: Adrienne Heinrich, Den Bosch (NL); Thomas Falck, Aachen (DE); Esther Marjan Van Der Heide, Hertogenbosh (NL); Yingrong Xie, Eindhoven (NL); Frank Mueller, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 842 days.

(21) Appl. No.: 15/518,512

(22) PCT Filed: Oct. 6, 2015

(86) PCT No.: PCT/EP2015/073040
§ 371 (c)(1),
(2) Date: Apr. 12, 2017

(87) PCT Pub. No.: WO2016/058866
PCT Pub. Date: Apr. 21, 2016

(65) Prior Publication Data
US 2017/0231531 A1 Aug. 17, 2017

(30) Foreign Application Priority Data
Oct. 13, 2014 (EP) ...................................... 14188581

(51) Int. Cl.
*A61B 5/11* (2006.01)
*G16H 40/63* (2018.01)
*A61B 5/00* (2006.01)

(52) U.S. Cl.
CPC .......... *A61B 5/1114* (2013.01); *A61B 5/0036* (2018.08); *A61B 5/0077* (2013.01);
(Continued)

(58) Field of Classification Search
CPC ..... A61B 5/1114; A61B 5/746; A61B 5/0077; A61B 5/1127; A61B 5/1115; A61B 5/1128; A61B 5/0033; G16H 40/63
See application file for complete search history.

(56) References Cited

U.S. PATENT DOCUMENTS

| 3,781,843 A | 12/1973 | Harrison et al. |
| 4,175,263 A | 11/1979 | Triplett et al. |

(Continued)

FOREIGN PATENT DOCUMENTS

| CN | 202282004 U | 6/2012 |
| CN | 102835958 A | 12/2012 |

(Continued)

OTHER PUBLICATIONS

J. Wang et al., "Adaptive Mean-Shift Tracking With Auxiliary Particles", in IEEE Transactions on Systems, Man and Cybernetics—Part B, vol. 39 (6), pp. 1578-1589 (2009).
(Continued)

*Primary Examiner* — Michael J Tsai
*Assistant Examiner* — Johnathan Maynard

(57) ABSTRACT

The invention provides a patient monitoring system for monitoring a patient in a bed. A video camera is used for capturing video images of the patient. Video analysis is used to determine and track the position of body parts of the patient including the hands. This analysis is enhanced by using sensors which detect interaction by the patient with pieces of equipment in the vicinity of the bed.

12 Claims, 4 Drawing Sheets

(52) U.S. Cl.
CPC ........... *A61B 5/1115* (2013.01); *A61B 5/1127* (2013.01); *A61B 5/1128* (2013.01); *A61B 5/746* (2013.01); *G16H 40/63* (2018.01)

(56) References Cited

U.S. PATENT DOCUMENTS

| | | | | |
|---|---|---|---|---|
| 5,140,309 | A | * | 8/1992 | Gusakov ............... G08B 21/22 340/573.4 |
| 8,131,012 | B2 | | 3/2012 | Eaton et al. |
| 2008/0021731 | A1 | | 1/2008 | Rodgers |
| 2009/0119843 | A1 | * | 5/2009 | Rodgers ................. G16H 40/67 5/611 |
| 2012/0075464 | A1 | * | 3/2012 | Derenne ................ H04N 7/185 348/135 |
| 2012/0089419 | A1 | | 4/2012 | Huster et al. |
| 2012/0330109 | A1 | | 12/2012 | Tran |
| 2013/0009761 | A1 | | 1/2013 | Horseman |
| 2013/0127620 | A1 | | 5/2013 | Siebers |
| 2014/0235969 | A1 | | 8/2014 | Van Der Heide |
| 2014/0249429 | A1 | | 9/2014 | Tran |
| 2014/0267718 | A1 | | 9/2014 | Govro |
| 2016/0038026 | A1 | | 2/2016 | Yang et al. |

FOREIGN PATENT DOCUMENTS

| | | |
|---|---|---|
| JP | H108257017 | 10/1996 |
| JP | 2000105885 | 4/2000 |
| JP | 2006223650 | 8/2006 |
| WO | 2007075701 | 7/2007 |
| WO | 2012/040554 | 3/2012 |

OTHER PUBLICATIONS

J. M. del Rincon et. al. "Tracking Human Position and Lower Body Parts Using Kalman and Particle Filters Constraine by Human Biomechanics" in IEEE Transactions on Systems, Man and Cybernetics—Part B, vol. 41 (1), pp. 26-37 (2010).

* cited by examiner

PATIENT MONITORING SYSTEM AND METHOD

CROSS REFERENCE TO RELATED APPLICATIONS

This application is the U.S. National Phase application under 35 U.S.C. § 371 of International Application No. PCT/EP2015/073040, filed Oct. 6, 2015, published as WO 2016/058866 on Apr. 21, 2016, which claims the benefit of European Patent Application Number 14188581.4 filed Oct. 13, 2014. These applications are hereby incorporated by reference herein.

FIELD OF THE INVENTION

This invention relates to the monitoring of patients, particularly when they are in a bed for treatment, for example a hospital bed.

BACKGROUND OF THE INVENTION

Conventionally, the motoric behavior of a hospital patient is observed when a member of the medical staff visits the patient. Detection of a change in the motoric behavior between the previous and current visit is often difficult to notice by medical staff. Especially in busy times it is difficult to recall the earlier observations. This type of inspection introduces non-negligible lag in the detection of critical problems, such as the onset of diseases revealed by change in motoric behavior or critical situations induced by the patients' movements.

Automatic video-based monitoring of patients has been proposed to address this issue. It is a relatively new topic and the developed tools are at their infancy.

Camera-based video monitoring is a promising approach and offers the opportunity for automatic detection of a change in the clinical condition. In theory, it allows full body motion analysis in an unobtrusive way. Continuous and automatic video monitoring is thus believed to offer the opportunity to provide enhanced information compared to body worn sensors.

In order to recognize and classify patient movements, features of natural and of unusual movements can be extracted from video images and they can then be provided to a classifier. Feature extraction for patient monitoring is commonly performed globally, based on movements of the entire body. However, movement classification based on specific body parts can provide even more meaningful information, as particular movements are often performed by specific body parts (e.g., moving the head continuously from left to right is unusual, whereas a repetitive hand movement while eating is not).

Video analysis methods have to cope with the dynamic aspects of the hospital environment. These can give rise to scene variations such as changes in the bed angle and bed backrest tilt, persons or objects like the TV screen occluding parts of the patient, different patient lying positions in bed, and a blanket covering body parts of the patient. These challenges make it difficult to include typical body segmentation methods and identification of body parts for patient monitoring.

For example, the presence of a blanket makes it difficult to fit a human model on the lying patient. Scene variations also limit current video analysis methods for body part segmentation (such as edge/gradient analysis, luminance value analysis, and object detection).

Sensors other than the video camera have also been suggested for monitoring the patients' motoric behavior. Generally, they are specialized sensors to detect a particular incident (e.g., a patient falling out of bed). While specialized sensors can be used for detecting specific events, video data is much richer in information. If the problems associated with video recognition identified above can at least partly be resolved, it gives the possibility to detect the patient's face and hands, and to analyze movements and interaction with objects, or recognize general behavior. Therefore, a video sensor system offers the opportunity to automatically analyze and recognize different types of movements performed by the patient, if the problems of scene variations and occlusion can be addressed.

It has also been recognized that monitoring the movement of a patient, or specific body parts of a patient such as the hands, can give information about a patient's clinical condition. For example, in addition to monitoring when a patient falls out of bed, there is a lot of additional relevant information for medical staff which can be extracted from patient movements. One example is an indication that a patient is pulling on medical equipment (for example the endotracheal tube or feeding tube). Some patient movements are disease-specific, such as grabbing in the air, or repetitive movement of legs in the case of delirium, or epileptic seizures, etc.

As mentioned above, there are various systems which aim to detect if a patient is getting out of bed, or is at risk of falling out of bed. For example, WO 2012/040554 discloses a camera based patient monitoring system, which has one aim of detecting when a patient is about to get out of bed. Equipment settings for equipment in the patient room may also be monitored, for example to detect if bed side rails are up or down.

These systems provide limited information, and do not for example enable patient movements which may be indicative of particular medical conditions to be identified. Thus, while it is known to use additional sensors in addition to a video monitoring system, there are still problems in using the video monitoring system in the environment of a bed-bound patient.

SUMMARY OF THE INVENTION

The invention is defined by the claims.

Examples according to an aspect of the invention provide a patient monitoring system for monitoring a patient in a bed, comprising:

a video camera for capturing video images of the patient;

a video analysis subsystem for determining and tracking the position of body parts of the patient including the hands;

a set of sensors associated with pieces of equipment in the vicinity of the bed, for detecting interaction by the patient, wherein the sensor signals are provided to the video analysis subsystem to assist in determining and tracking the position of the body parts of the patient.

This system makes use of the knowledge of the location of the body parts of the patient, such as the hand and arm, as well as the knowledge of the position of equipment with which the patient may interact. This additional interaction information can be used to help in classifying unusual from natural movements. For example, interacting with an entertainment screen is natural, whereas continuously pulling on medical equipment can be unusual. Grabbing in the air repetitively may even be indicative of particular medical conditions.

The pieces of equipment may be fixed in position, in which case their position is known to the video analysis subsystem during a configuration process. They may instead be movable, such as a display screen. In this case, the location of the pieces of equipment may also be tracked by the video analysis subsystem, or their real-time positions may be provided to the video system by other methods.

When there is interaction by the patient, based on the known locations of the objects with which the patient is interacting, it is then possible to identify the image areas where the hands and arms are located. This can be used to aid in tracking them and analyzing repetitive hand and arm movements in real time or subsequently.

In this way, a connected system is defined in which the hospital (or other caregiving institution) room facilities can communicate with a video monitoring system. These facilities for example may include a screen, bed rails, and medical devices such as sensors on the patient body, tubes, and intravenous lines.

The video analysis subsystem may for example be adapted to identify video image regions in which patient body parts are located, based on the sensor signals. In this way the video analysis subsystem can increase the confidence with which hand or arm (or other body part) locations can be correctly tracked.

The set of sensors may comprise:
a touch sensor for detecting when a display screen has been touched by the patient.

Repeated back and forth movement of the patient's hands near the screen may then be classified as normal behavior, for example for a touch screen or when adjusting the screen position or settings.

The set of sensors may comprise:
a touch sensor for detecting when a bed hand rail has been touched by the patient.

This can be used to provide a warning that the patient may be trying to get out of bed, but additionally it enables the location of a hand of the patient to be assumed as in the area of the hand rail, again to improve the reliability of the body part detection.

The set of sensors may comprise:
a finger clip sensor for example for pulse oximetry (SpO2).

The set of sensors may comprise:
a sensor for detecting when a drug or breathing air delivery system has been touched by the patient.

This may be used to detect grabbing by the patient of their supply lines, which can generate a warning.

This list of possible sensors is not exhaustive. Indeed, sensors from any connected device or object could be used to detect that the patient interacts with the device or object, such as cups, bottles and switches.

The video analysis subsystem is preferably adapted to create an alert based on the video analysis, when the movement of the patient body parts is deemed abnormal or presents a danger.

The video analysis subsystem is for example for determining and tracking the position of body parts of the patient including the arms and legs. Thus, there may be tracking of the arms and/or legs in addition to the hands.

Examples in accordance with another aspect of the invention provide a patient monitoring method for monitoring a patient in a bed, comprising:
capturing video images of the patient;
using video analysis to determine and track the position of body parts of the patient including the hands;
detecting interaction by the patient with pieces of equipment in the vicinity of the bed; and
using the detected interaction in the video analysis to assist in determining and tracking the position of the body parts of the patient.

This method uses information about patient interaction with equipment in the vicinity of the patient to improve the performance of a video analysis subsystem, and to enable an increased amount of useful information to be derived from the video analysis. The video analysis subsystem is for example used to identify video image regions in which patient body parts are located, based on the detected interaction.

Detecting interaction may comprise detecting when a display screen has been touched by the patient, or detecting when a bed hand rail has been touched by the patient, or detecting when a drug delivery system has been touched by the patient.

The method may further comprise detecting the presence of people other than the patient based on detected interactions with pieces of equipment. These other people can be nurses or guests. This information can further assist in the tracking and localizing of the patient.

The invention also provides a computer program comprising computer program code means adapted to perform the method when said computer program is run on a computer. The computer program can be embodied on a computer readable medium.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a patient monitoring system for monitoring a patient in a bed. A video camera is used for capturing video images of the patient. Video analysis is used to determine and track the position of body parts of the patient including the hands. This analysis is enhanced by using sensors which detect interaction by the patient with pieces of equipment in the vicinity of the bed.

The invention can be applied to any care-giving establishment, or even to the provision of care in the home. By way of example only, the description below refers only to a hospital.

This approach means that hospital room facilities essentially communicate with the video monitoring system. By exchanging information between the facilities and the video monitoring system, more knowledge can be gained about the video content, for example where the patient screen is located, where the arms/hands are, where body sensors are placed within the video image.

This information can be used for classifying patient movements either as unusual or as natural. It can be used to enhance the identification of the location of hands and/or arms in the image and used for tracking those locations in future images. The end result is then improved classification of unusual or natural movements.

Figure 1:
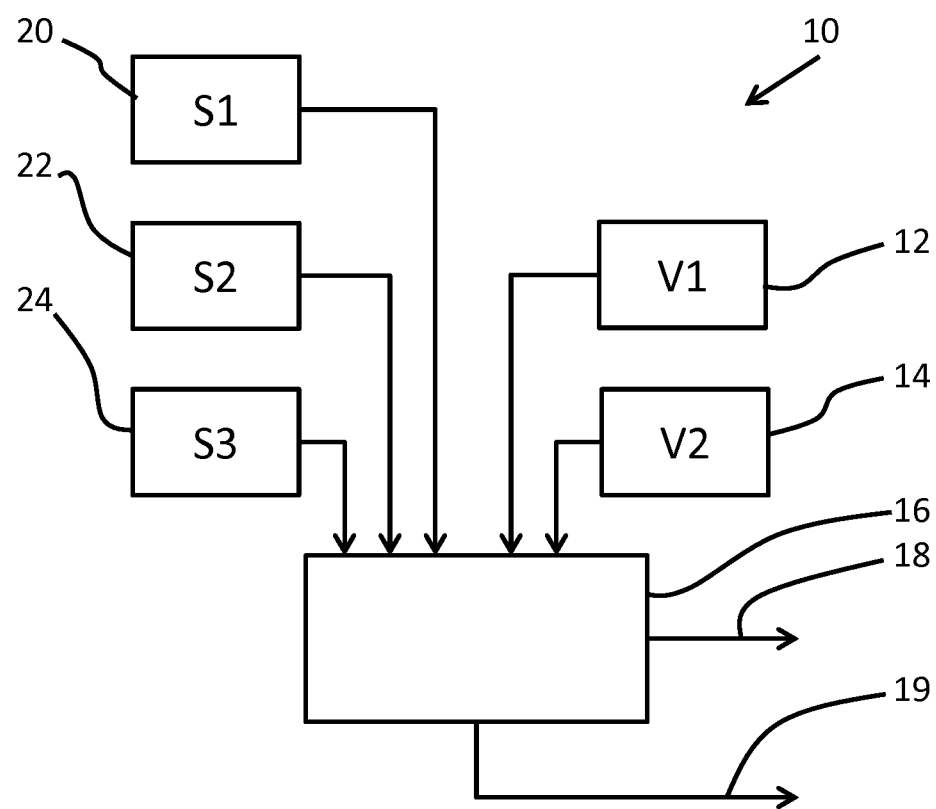
FIG. 1 shows a patient monitoring system in accordance with one example of the invention.

FIG. 1 shows a patient monitoring system 10 in accordance with one example of the invention.

The system comprises at least one video camera for capturing video images of a patient when they are in bed during a period of treatment. FIG. 1 shows two video cameras 12, 14. These provide their video output to a video analysis subsystem 16 for determining and tracking the position of body parts of the patient including the hands. This tracking information is provided as an output 18. This output can be in the form of tracking information to be interpreted. However, the system can additionally (or alternatively) internally generate an alert 19 based on the video analysis, when the movement of the patient body parts is deemed abnormal or presents a danger.

The video tracking algorithms used are conventional. For example, examples of video tracking algorithm are:

Mean-shift tracking (see e.g., J. Wang, and Y. Yagi, "Adaptive Mean-Shift Tracking With Auxiliary Particles", in IEEE Transactions on Systems, Man and Cybernetics—Part B, Vol. 39 (6), pp. 1578-1589 (2009)); and Kalman and particle filters (see e.g. J. M. del Rincon et. al. "Tracking Human Position and Lower Body Parts Using Kalman and Particle Filters Constrained by Human Biomechanics" in IEEE Transactions on Systems, Man and Cybernetics—Part B, Vol. 41 (1), pp. 26-37 (2010).

In order to improve the performance of the video analysis subsystem, a set of sensors 20, 22, 24 associated is provided. Each sensor is associated with a piece of equipment in the vicinity of the bed, for detecting interaction by the patient. The sensor signals are provided to the video analysis subsystem to assist in determining and tracking the position of the body parts of the patient.

The sensors provide their output to the video tracking algorithm without any modification. The video tracking system then includes a fusion block which combines the video data and the sensor data to process them together.

Figure 2:
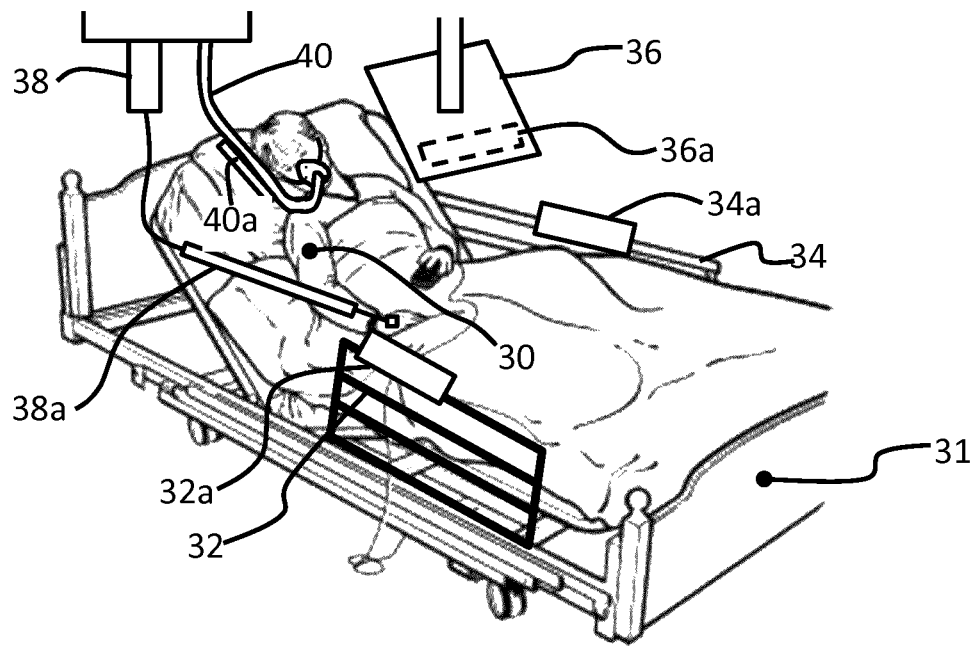
FIG. 2 shows the system in use for a hospital bed.

FIG. 2 shows the system in use. A patient 30 is shown in a hospital bed 31. Various pieces of equipment are in the vicinity of the patient, including bed side rails 32, 34, an entertainment screen 36, a drug delivery system 38 and a breathing gas delivery system 40. Each of these is associated with a respective sensor 32a, 34a, 36a, 38a, 40a. These sensors detect interaction by the user. They may for example comprise touch sensors, for example using capacitive touch sensing.

However, different sensors can be used for different pieces of equipment. For example, for the entertainment screen 36, the sensing may be based on control signals provided by the screen, which indicate that changes in settings have been made to the screen, such as channel changes, contrast or brightness changes or any other user-input alterations. A touch sensor may also be used in connection with the screen, for example to indicate when adjustment of the screen position is being made by the patient.

The sensors for the drug delivery system 38 or breathing air delivery system 40 may for example be based on force sensing of a detected pulling force, which again indicates that the patient is interacting with the system.

As shown in FIG. 1, the sensor information is provided to the video analysis subsystem 16.

Some of the equipment will have a fixed location, so that detection of the interaction of the patient with the equipment can for example be used to provide an approximate hand location to the video analysis subsystem. The fixed location can be programmed in to the system as part of an installation procedure. For equipment that is movable, such as the screen 36, the location may be updated in real time. For example, the video processing can easily identify the screen location based on its characteristic size and shape.

There may be markers such as QR codes ("Quick Response" 2D barcodes) on the equipment to help the video analysis subsystem recognize certain type of equipment. Other tracking systems may be used to determine the location of objects, such as RFID sensing.

The sensors may also issue alerts based on out-of-the-ordinary signal behaviors from the sensors. These may provide information which is not specifically aimed at detecting patient interaction but which is used for other monitoring purposes. For example, sensors including finger clips or ECG electrodes may be provided. If a sensor, such as ECG electrodes, detects behavior which is abnormal, this may be due to patient interaction (pulling on the electrodes) or it may be due to a medical problem such as abnormal heart behavior. By flagging this incident, the video system can be alerted that something may be happening in the vicinity of the respective sensor, so that video images can be analyzed.

When a sensor indicates that there has been interaction with an equipment item, and the information has been transmitted to the video system, the video system can then check where in the image movement has taken place. Movement is expected to be present close to the equipment item. If grayscale/histogram/edge/SIFT (Scale Invariant Feature Transform) feature properties or other image features are not sufficient to identify the equipment, frame differencing with other frames (where no movement was present) should return a high detection rate around the new location. In this way, it is possible to refine the location information even if a portable item had been at another location before.

The system thus makes use of the knowledge of the location of the body parts of the patient, such as the hand and arm, as well as the knowledge of the position of equipment with which the patient may interact.

If the patient is making repeated movements in the vicinity of the screen, this may be perfectly normal. If the patient is making repeated movements in the air or in the vicinity of the drug or breathing air delivery systems, this may be more cause for alarm.

Figure 3:
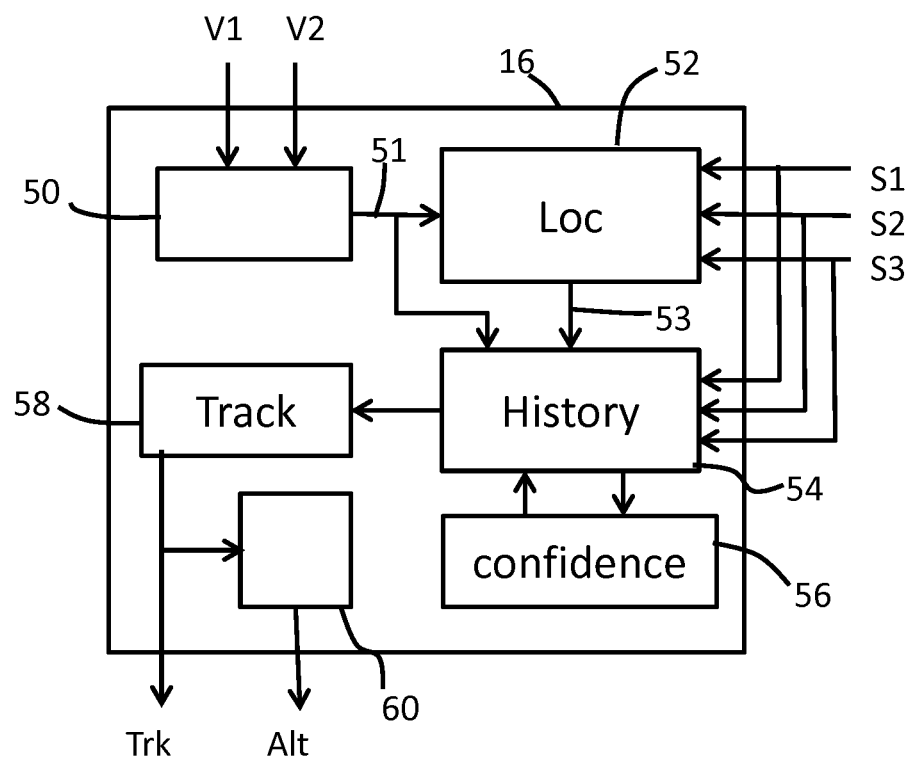
FIG. 3 show in more detail the video signal processing.

FIG. 3 shows one example of the functions implemented by the video analysis subsystem 16. The system in this example is for determining and tracking the locations of the hands and arms in the video images.

The video signals V1 and V2 are provided to a motion estimation or detection system 50. This provides motion detection information 51 to a localization unit 52 which identifies the regions of the video where the detected motion is taking place. The system 50 can also include computer vision techniques for identifying hands or other body parts in the video images, to supplement the information from the sensors. The region information is shown as 53 which relates to regions where motion has taken place or where there is identification of particular body parts. The localization unit also receives as inputs the sensor signals S1, S2, S3. When the patient interacts with a piece of equipment in the vicinity of the patient, the associated sensor signals to the connected network indicating that it has been touched or otherwise used.

The motion detection information 51 as well as the localization information 53 relating to the corresponding video images can then be processed more efficiently based on the known locations of the hands, for interactions which are known to take place with the hands.

This approach enables the hands (for example) to be detected with a high confidence and then enables them to be tracked. Their motion behavior can then be analyzed to come to the conclusion if the movement is unusual or natural. Knowing when an equipment item is touched gives information on where the hands are which can then be identified in the image with e.g. motion detection.

The use of additional sensor input also means that the system can detect when another person (e.g. nurse) is in the image. For example, if the button of a bedside monitor is pressed, it can be concluded that a nurse is in the room. Knowing the location of the bedside monitor in the room, movements of the nurse can be excluded from the analysis of the movements caused by the patient.

Thus, the system and method may comprise detecting the presence of people other than the patient based on detected interactions with pieces of equipment. In general this can be implemented by having sensors outside the patient area (i.e. not reachable by a patient lying in bed). A person other than the patient is probably in the image when these sensors are activated, and the movements from these other person(s) can be ignored.

A movement history unit 54 stores the localization information 53, the motion detection information 51 as well as the sensor signals over time. This allows for tracking, updating locations and enables repetitive movements to be recognized. This enables the confidence of the correct detection of hand or arm locations to be increased. This can be used to make the system more robust when computing the hand or arm locations. Unit 56 provides an update of the confidence of the hand or arm area, which shows how reliable the detection result can be considered to be.

For example, when an interaction with an equipment item is signaled, the confidence is high that the image area where the hands are present can be found. Afterwards, the hands are being tracked and movements analyzed. In the subsequent processing steps, the location of the hands may become less accurate. When another interaction has been signaled, and the tracking of hands results in hands being present in the image area close to the device, there is again high confidence that hand movements between the two interactions have been correctly found.

Once locations have been established, the hands and/or arms can be tracked by unit 58. This generates a hand or arm tracking signal Trk. This can be interpreted to generate an alert Alt by an interpreting unit 60. The information on hand or arm locations can thus be used to improve the automatic classification algorithm of unusual movement which will generate an alert, while natural movements will be ignored. In particular, more detailed information on the hand locations is known and better tracking can be carried out.

Knowledge about the device with which the user is interacting and the type of interaction can benefit in classifying natural or unusual movements by the interpretation unit 60. Some devices are more likely to be interacted with than others in a natural condition. For example, writing an email via computer screen will give a typical movement pattern which can be recognized.

Figure 4:
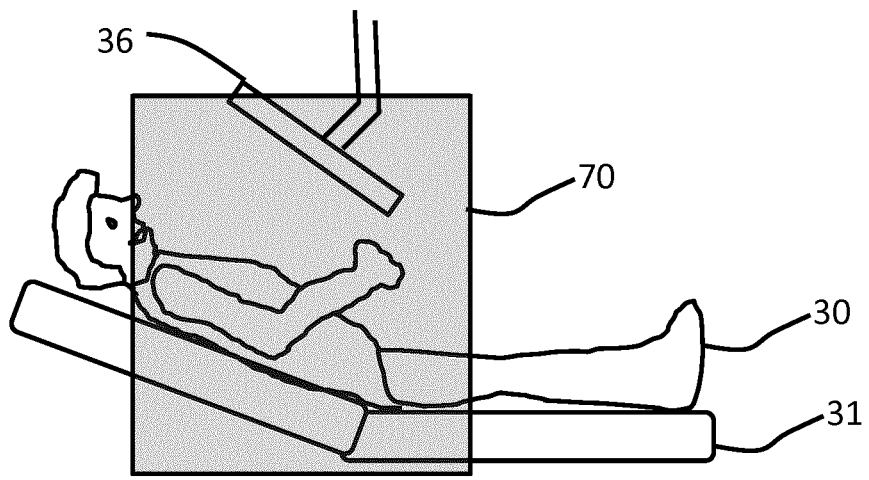
FIGS. 4 to 6 show different steps during use of the system.
Figure 5:
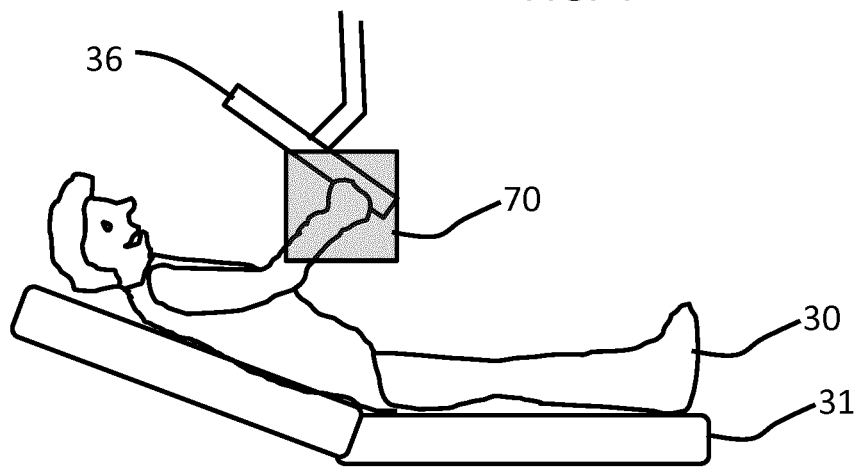
Figure 6:
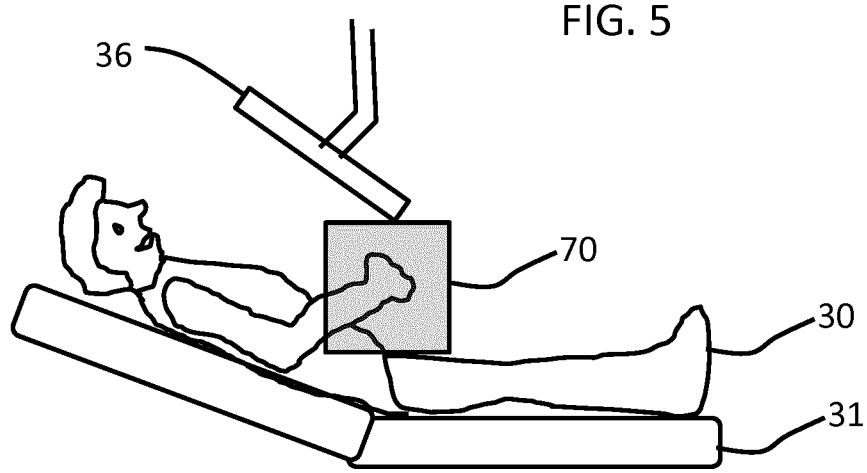

FIGS. 4 to 6 show graphically the method used. They show the patient 30 in bed 31 with a display 36 over the patient.

In FIG. 4, the arms of a patient 30 are moving, but there is no interaction with the screen yet. The region 70 shows the area in which movement is detected by the video analysis subsystem. In FIG. 5, the patient's hand touches the screen, and the screen communicates that it has been touched to the video analysis subsystem.

Moving areas in the video image can be identified and based on past movements, the area of the hand and the area of the screen (if the screen is moved) can be identified with greater accuracy and/or confidence as shown by the reduced area 70. In FIG. 6, subsequent tracking of the hand position is made more accurate, making use of the previous knowledge of hand and arm location.

It will be clear from the description above that the invention provides a system in which hospital room facilities communicate with a video monitoring system. The transfer of information regarding which device is being interacted with can help in subsequently automatically identifying the following information in the video images:

location of the medical equipment in the image;
location of entertainment facilities in the image;
location of hands and arms in the image, when the equipment is most likely to be operated using the hands and arms.

This may be used to provide improved classification of a current movement as unusual or as natural. The more accurate detection of hand or arm locations enables future tracking to be more reliable. This tracking then enables improved classification of unusual or natural movements based on the movements of the arms or hands.

The location of the equipment in the room may for example be initialized by staff by marking areas on a screen which present the video footage. Most of the time, the equipment in the room (except for medical equipment attached to the patient) is static and not moving. For example the screen will only be moved towards the patient or away from the patient at the start or end of the time he or she wants to use it. Thus, a template can be constructed from all equipment in the video-image automatically by using history of images and by checking for static parts.

When also taking into account the detected interaction with the sensors, the exact location of the equipment can be detected automatically.

Note that many additional types of sensor may be used. Indeed sensors can be provided on any device or object to detect when a patient interacts with the device or object. The possibility of interconnecting devices using uniquely identifiable embedded computing devices is known in the field of the technology known as the "Internet of things".

Clinical staff may need to interact with medical equipment such as intravenous lines, feeding tubes etc., for example, check correct attachment. Furthermore, the entertainment screen may be used not only by the patient but also by visitors or clinical staff helping the patient. To ensure that in these situations movements of others are not confused with movements of the patient, the movement history of clinical staff or other persons in the image can also be tracked and used.

The invention is applicable in patient monitoring systems for many different types of wards in a hospital (intensive care, acute care, general wards, geriatric wards). It can also be used in nursing homes or rehabilitation centers, and also in home health care monitoring systems.

Automatic and continuous video movement analysis may for example be used for early detection of delirium or other diseases with unusual movements or behaviors. Early warnings can be provided when a patient interacts with a medical device such as intravenous lines. Early detection can be provided of when patient is trying to get out of bed, for example based on interaction with the bed rail.

The video analysis can essentially be performed in software, which is run by a controller.

Figure 7:
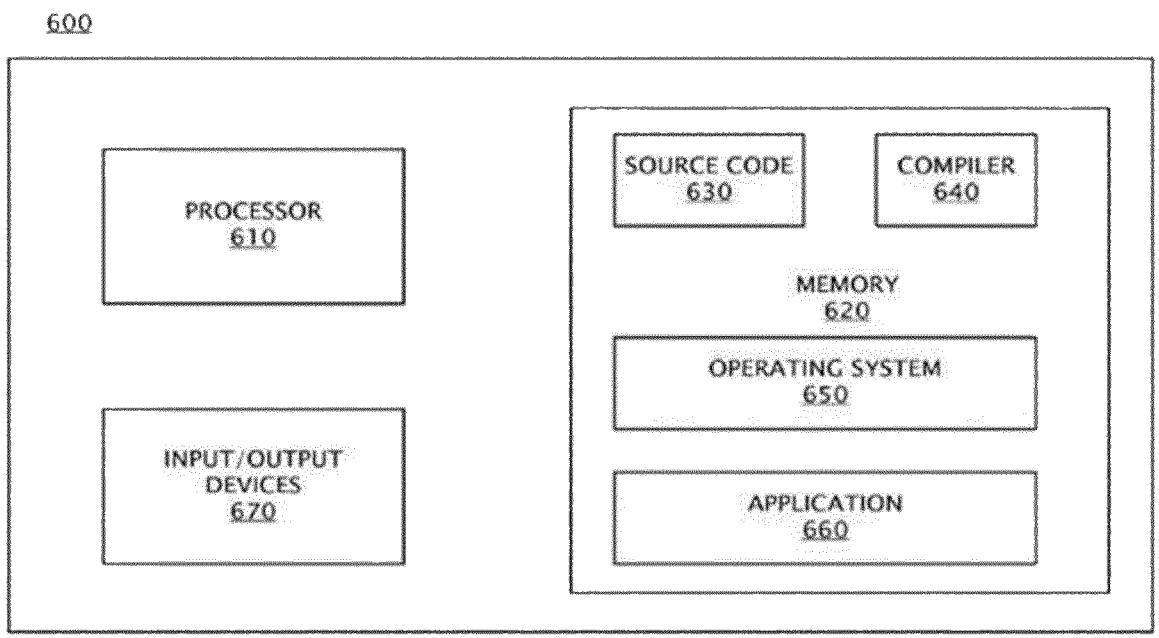
FIG. 7 shows a computer used for implementing the video recognition algorithm.

FIG. 7 illustrates an example of how a computer 600 may be used. Various operations discussed above may utilize the capabilities of the computer 600.

The computer 600 may comprise, but is not limited to, PCs, workstations, laptops, PDAs, palm devices, servers, storages, and the like. Generally, in terms of hardware architecture, the computer 600 may include one or more processors 610, memory 620, and one or more I/O devices 670 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 610 is a hardware device for executing software that can be stored in the memory 620. The processor 610 can be virtually any custom made or commercially available processor, a central processing unit (CPU), a digital signal processor (DSP), or an auxiliary processor among several processors associated with the computer 600, and the processor 610 may be a semiconductor based microprocessor (in the form of a microchip) or a microprocessor.

The memory 620 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 620 may incorporate electronic, magnetic, optical, and/or other types of storage media. Note that the memory 620 can have a distributed architecture, where various components are situated remote from one another, but can be accessed by the processor 610.

The software in the memory 620 may include one or more separate programs, each of which comprises an ordered listing of executable instructions for implementing logical functions. The software in the memory 620 includes a suitable operating system (O/S) 650, compiler 640, source code 630, and one or more applications 660 in accordance with exemplary embodiments. As illustrated, the application 660 comprises numerous functional components for implementing the features and operations of the exemplary embodiments. The application 660 of the computer 600 may represent various applications, computational units, logic, functional units, processes, operations, virtual entities, and/or modules in accordance with exemplary embodiments, but the application 660 is not meant to be a limitation.

Application 660 may be a source program, executable program (object code), script, or any other entity comprising a set of instructions to be performed. When a source program, then the program is usually translated via a compiler (such as the compiler 640), assembler, interpreter, or the like, which may or may not be included within the memory 620, so as to operate properly in connection with the O/S 650.

The I/O devices 670 may include input devices such as, for example but not limited to, a mouse, keyboard, scanner, microphone, camera, etc. Furthermore, the I/O devices 670 may also include output devices, for example but not limited to a printer, display, etc.

The application 660 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A video analysis subsystem for use in a patient monitoring system for monitoring a patient in a bed, the video analysis subsystem comprising:
    means for receiving video images of the patient captured by a video camera;
    means for receiving sensor signals obtained from a set of sensors associated with pieces of equipment located in the vicinity of the bed for detecting interaction by the patient;
    means for determining and tracking the position of body parts of the patient from the video images and the sensor signals; and means for classifying movement of the body parts of the patient as abnormal based upon an automatic classification algorithm that uses the video images and the sensor signals to distinguish unusual movements from natural movements based upon prior tracking of the position of the body parts of the patient.

2. A patient monitoring system for monitoring a patient in a bed, comprising:
- a video camera configured to capture video images of the patient;
- a set of sensors, associated with pieces of equipment in the vicinity of the bed, configured to detect interaction by the patient and obtain sensor signals,
- a video analysis subsystem, as claimed in claim 1, configured to determine and track for the position of body parts of the patient from the video images and the sensor signals.

3. A video analysis subsystem as claimed in claim 1, wherein the video analysis subsystem is configured to identify video image regions in which the patient body parts are located, based on the sensor signals.

4. A patient monitoring system as claimed in claim 2, wherein the set of sensors comprises one or more of:
- a touch sensor configured to detect when a display screen has been touched by the patient;
- a touch sensor configured to detect when a bed handrail has been touched by the patient;
- a finger clip sensor; and
- a sensor configured to detect when a drug or breathing air delivery system has been touched by the patient.

5. A video analysis subsystem as claimed in claim 1, wherein the video analysis subsystem is configured to create an alert based on the video analysis after the movement of the body parts of the patient is deemed abnormal or presents a danger.

6. A video analysis subsystem as claimed in claim 1, wherein the video analysis subsystem is configured to determine and track the position of the body parts of the patient including one or more of the hands, the arms, and the legs.

7. A patient monitoring method for monitoring a patient in a bed, the patient monitoring method comprising:
- capturing video images of the patient;
- detecting interaction by the patient with pieces of equipment in the vicinity of the bed and obtaining sensor signals with a set of sensors associated with pieces of equipment in the vicinity of the bed;
- determining and tracking the position of body parts of the patient from the video images and the sensor signals; and
- classifying movement of the body parts of the patient as abnormal based upon an automatic classification algorithm that uses the video images and the sensor signals to distinguish unusual movements from natural movements based upon prior tracking of the position of the body parts of the patient.

8. A video analysis method for use in a patient monitoring system for monitoring a patient in a bed, the video analysis method comprising:
- receiving video images of the patient captured by a video camera;
- receiving sensor signals obtained from a set of sensors associated with pieces of equipment located in the vicinity of the bed for detecting interaction by the patient;
- determining and tracking the position of body parts of the patient from the video images and the sensor signals; and classifying movement of the body parts of the patient as abnormal based upon an automatic classification algorithm that uses the video images and the sensor signals to distinguish unusual movements from natural movements based upon prior tracking of the position of the body parts of the patient.

9. The patient monitoring method as claimed in claim 7, wherein detecting interaction comprises one or more of:
- detecting when a display screen has been touched by the patient;
- detecting when a bed handrail has been touched by the patient; and
- detecting when a drug or breathing air delivery system has been touched by the patient.

10. The patient monitoring method as claimed in claim 7, further comprising:
- detecting the presence of people other than the patient based on detected interactions with pieces of equipment.

11. The video analysis method as claimed in claim 8, further comprising:
- creating an alert based on the video analysis after the movement of the body parts of the patient is deemed abnormal or presents a danger.

12. The video analysis method as claimed in claim 8, wherein the video analysis is used to identify video image regions in which patient body parts are located, based on the detected interaction.

* * * * *